United States Patent
Johnston et al.

(10) Patent No.: US 8,583,245 B1
(45) Date of Patent: Nov. 12, 2013

(54) METHODS AND SYSTEMS FOR ARCHIVING PATIENT DATA USED TO FIT A COCHLEAR IMPLANT SYSTEM TO A PATIENT

(75) Inventors: Jacob Johnston, Winnetka, CA (US); Fernando Chapa, Harold, CA (US); Guillermo A. Calle, Moorpark, CA (US)

(73) Assignee: Advanced Bionics AG, Zug (CH)

( * ) Notice: Subject to any disclaimer, the term of this patent is extended or adjusted under 35 U.S.C. 154(b) by 741 days.

(21) Appl. No.: 12/847,095

(22) Filed: Jul. 30, 2010

(51) Int. Cl.
  *A61N 1/36* (2006.01)
(52) U.S. Cl.
  USPC .............................. 607/56; 607/137
(58) Field of Classification Search
  USPC ............................. 607/55–57, 137
  See application file for complete search history.

(56) References Cited

U.S. PATENT DOCUMENTS

| | | | | |
|---|---|---|---|---|
| 5,626,629 | A | * | 5/1997 | Faltys et al. ............ 607/57 |
| 5,785,660 | A | * | 7/1998 | van Lake et al. ........ 600/523 |
| 2001/0014611 | A1 | * | 8/2001 | Dufort ................. 455/517 |

\* cited by examiner

*Primary Examiner* — Brian T Gedeon
(74) *Attorney, Agent, or Firm* — ALG Intellectual Property, LLC (57) ABSTRACT

An exemplary method includes a fitting subsystem maintaining a plurality of patient data instances associated with a fitting of a cochlear implant system to a patient, displaying one or more of the patient data instances within one or more main views of a graphical user interface used to fit the cochlear implant system to the patient, receiving data representative of a request by a user to archive a patient data instance included in the plurality of patient data instances, and archiving, in response to the request, the patient data instance by preventing the patient data instance from being displayed within the one or more main views of the graphical user interface. Corresponding methods and systems are also described.

17 Claims, 11 Drawing Sheets

METHODS AND SYSTEMS FOR ARCHIVING PATIENT DATA USED TO FIT A COCHLEAR IMPLANT SYSTEM TO A PATIENT

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant of a cochlear implant system is initially implanted in a patient, and during follow-up tests and checkups thereafter, it is usually necessary to fit the cochlear implant system to the patient. Fitting of a cochlear implant system to a patient is typically performed by an audiologist or the like who utilizes a fitting system to present various stimuli to the patient and relies on subjective feedback from the patient as to how such stimuli are perceived.

During a fitting procedure, patient data specific to a particular cochlear implant patient is used and/or acquired by the fitting system. Such data may include personal information associated with the patient, data representative of one or more sound processing programs associated with the patient, and/or any other type of data specific to the patient.

At times, it may be desirable to remove various instances of patient data associated with a cochlear implant patient from a fitting system. For example, it may be desirable to remove data representative of a sound processing program that a patient no longer uses from a fitting system. However, various rules and regulations may mandate that patient data be retained for the purposes of record keeping, traceability, accountability, etc.

SUMMARY

An exemplary method includes a fitting subsystem 1) maintaining a plurality of patient data instances associated with a fitting of a cochlear implant system to a patient, 2) displaying one or more of the patient data instances within one or more main views of a graphical user interface used to fit the cochlear implant system to the patient, 3) receiving data representative of a request by a user to archive a patient data instance included in the plurality of patient data instances, and 4) archiving, in response to the request, the patient data instance by preventing the patient data instance from being displayed within the one or more main views of the graphical user interface.

Another exemplary method includes a fitting subsystem 1) maintaining a plurality of program data instances representative of a plurality of sound processing programs associated with a cochlear implant patient, 2) displaying one or more of the program data instances in a program view of a graphical user interface, 3) selecting a program data instance displayed in the program view of the graphical user interface in response to a user input selection command, 4) receiving data representative of a request by the user to archive the selected program data instance, and 5) archiving, in response to the request to archive, the selected program data instance by removing the selected program data instance from being displayed within the program view of the graphical user interface.

An exemplary system includes a storage facility, a user interface facility, and an archive facility communicatively coupled one to another. The storage facility is configured to maintain a plurality of patient data instances associated with a fitting of a cochlear implant system to a patient. The user interface facility is configured to display one or more of the patient data instances within one or more main views of a graphical user interface used to fit the cochlear implant system to the patient. The archive facility is configured to receive data representative of a request by a user to archive a patient data instance included in the plurality of patient data instances and archive, in response to the request, the patient data instance by preventing the patient data instance from being displayed within the one or more main views of the graphical user interface.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for archiving patient data used to fit a cochlear implant system to a patient are described herein. As described in more detail below, a fitting subsystem may be configured to maintain a plurality of patient data instances associated with a fitting of a cochlear implant system to a patient, display one or more of the patient data instances within one or more main views of a graphical user interface used to fit the cochlear implant system to the patient, receive data representative of a request by a user to archive a patient data instance included in the plurality of patient data instances, and archive, in response to the request, the patient data instance by preventing the patient data instance from being displayed within the one or more main views of the graphical user interface. The archived patient data instance may be subsequently displayed and accessed in an archive view separate from the one or more main views of the graphical user interface.

As used herein, the term "patient data" refers to data descriptive of or otherwise associated with one or more cochlear implant patients. Patient data may include, but is not limited to, patient record data descriptive of one or more characteristics of a patient (e.g., the patient's name, age, contact information, etc.), program data representative of one or more sound processing programs and/or control parameters associated with a patient, control parameter data representative of one or more control parameters associated with a patient, measurement data representative of one or more measurements performed by a cochlear implant system associated with a patient, and/or any other data specific to a particular patient. A "patient data instance" refers to one or more instances or portions of patient data. For example, a patient data instance may refer to a portion of patient data associated with a particular sound processing program, patient record, etc.

Numerous advantages may be associated with the methods and systems described herein. For example, by archiving patient data instances, as opposed to permanently deleting them, the patient data instances may be maintained without undesirably cluttering one or more main views of a graphical user interface used to fit a cochlear implant system to a patient. Archived patient data instances may still be accessed (e.g., viewed, edited, and/or used in a fitting procedure) by directing the fitting subsystem to display the archived patient data instances in an archive view of the graphical user interface.

Figure 1:
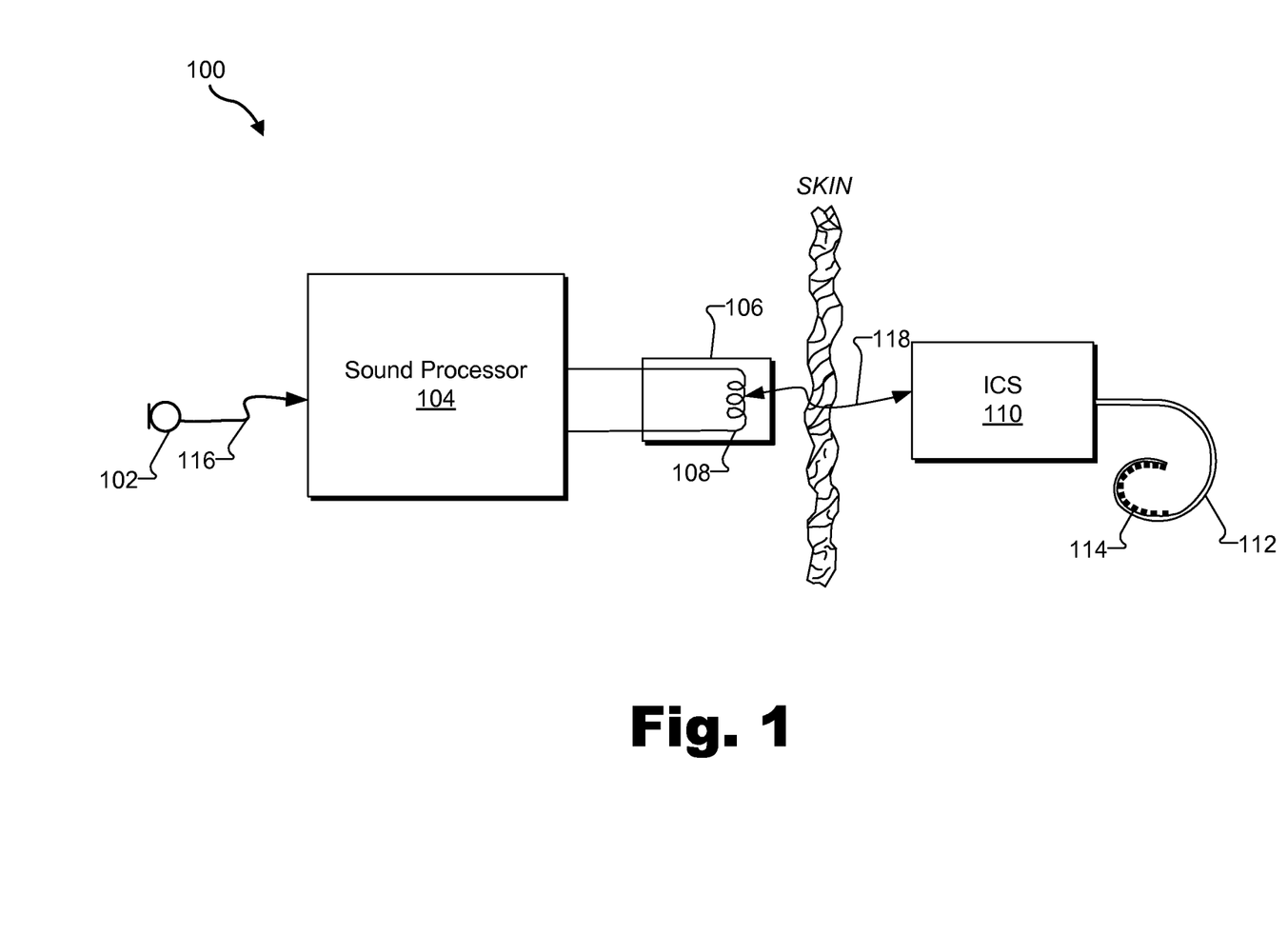
FIG. 1 illustrates an exemplary cochlear implant system according to principles described herein.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, an implantable cochlear stimulator ("ICS") 110, and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented by a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to implantable cochlear stimulator 110 with coil 108 by way of a communication link 118. These control parameters may be configured to specify one or more stimulation parameters, operating parameters, and/or any other parameter by which implantable cochlear stimulator 110 is to operate as may serve a particular implementation. Exemplary control parameters include, but are not limited to, stimulation current levels, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 118. It will be understood that data communication link 118 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 114 disposed along lead 112. In some examples, implantable cochlear stimulator 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by implantable cochlear stimulator 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
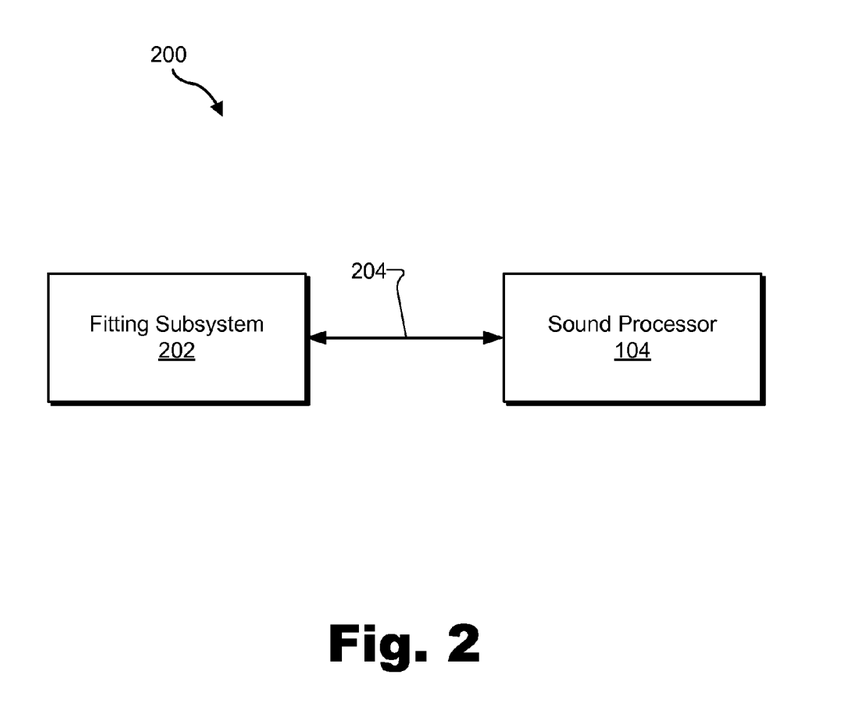
FIG. 2 illustrates an exemplary cochlear implant fitting system according to principles described herein.

FIG. 2 illustrates an exemplary cochlear implant fitting system 200 (or simply "fitting system 200") that may be used to fit sound processor 104 to a patient. As used herein, the terms "fitting a sound processor to a patient" and "fitting a cochlear implant system to a patient" will be used interchangeably to refer to performing one or more fitting operations associated with sound processor 104 and/or any other component of cochlear implant system 100. Such fitting operations may include, but are not limited to, adjusting one or more control parameters by which sound processor 104 and/or implantable cochlear stimulator 110 operate, measuring one or more electrode impedances, performing one or more neural response detection operations, and/or performing one or more diagnostics procedures associated with the cochlear implant system.

As shown in FIG. 2, fitting system 200 may include a fitting subsystem 202 configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. An exemplary implementation of fitting subsystem 202 will be described in more detail below.

Figure 3:
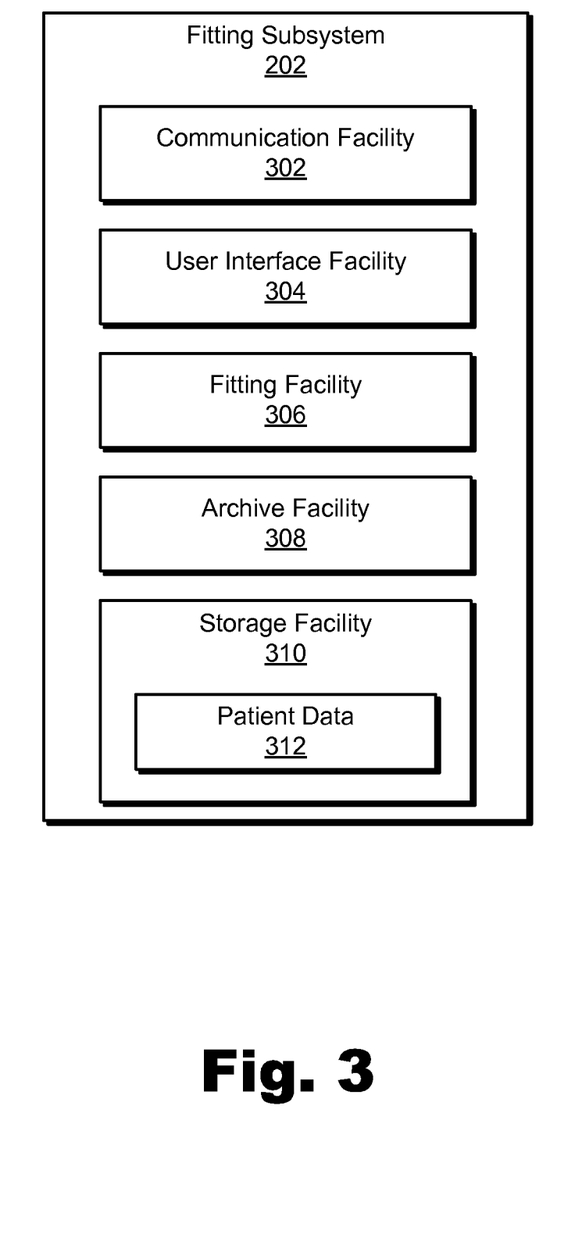
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, an archive facility 308, and a storage facility 310, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

Communication facility 302 may additionally or alternatively be configured to facilitate communication between fitting subsystem 302 and one or more other devices. For example, communication facility 302 may be configured to facilitate communication between fitting subsystem 302 and one or more computing devices (e.g., by way of the Internet and/or one or more other types of networks), reference implants, and/or any other computing device as may serve a particular implementation.

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display.

As will be described in more detail below, user interface facility 304 may be configured to display one or more patient data instances within one or more main views of a graphical user interface used to fit a cochlear implant system to a patient. User interface facility 304 may be further configured to display one or more archived patient data instances within an archive view of the graphical user interface used to fit the cochlear implant system to the patient. As used herein, a "main view" refers to any view within a graphical user interface in which one or more non-archived patient data instances may be displayed and an "archive view" refers to any view separate from a main view of a graphical user interface in which one or more archived patient data instances may be displayed. Exemplary main views and archive views will be described in more detail below.

Fitting facility 306 may be configured to perform one or more of the fitting operations described herein. For example, fitting facility 306 may be configured to adjust one or more control parameters by which sound processor 104 and/or implantable cochlear stimulator 110 operate, direct sound processor 104 to measure one or more electrode impedances, perform one or more neural response detection operations, and/or perform one or more diagnostics procedures associated with cochlear implant system 100. As will be described in more detail below, fitting facility 306 may use one or more patient data instances and/or one or more archived patient data instances to perform one or more fitting operations described herein.

In some examples, fitting facility 306 may be configured to selectively use one or more sound processing programs to fit sound processor 104 to a patient. As used herein, a "sound processing program" refers to any program that is executable by sound processor 104. Hence, a sound processing program may specify a particular mode in which sound processor 104 is to operate. For example, a sound processing program may define a set of control parameters selected to optimize a listening experience of a cochlear implant patient in a particular listening environment (e.g., a relatively quiet room, a noisy restaurant, a musical environment, etc.). Other sound processing programs may be configured to facilitate measurement of one or more electrode impedances, performance of one or more neural response detection operations, and/or performance of one or more diagnostics procedures associated with cochlear implant system 100.

Archive facility 308 may be configured to perform one or more archive operations on one or more patient data instances. For example, archive facility 308 may be configured to receive data representative of a request by a user to archive a patient data instance included in a plurality of patient data instances maintained by storage facility 310 and, in response to the request, archive the patient data instance by preventing the patient data instance from being displayed within the one or more main views of the graphical user interface displayed by user interface facility 304.

In some examples, archive facility 308 may be further configured to receive data representative of a request by a user to unarchive an archived patient data instance. In response to the request, archive facility 308 may unarchive the archived patient data instance by removing the patient data instance from the archive view of the graphical user interface and allowing the patient data instance to be displayed within the one or more main views of the graphical user interface.

Storage facility 310 may be configured to maintain patient data 312, which may include one or more patient data instances and/or one or more archived patient data instances associated with one or more cochlear implant patients. Storage facility 310 may be configured to maintain additional or alternative data as may serve a particular implementation.

Figure 4:
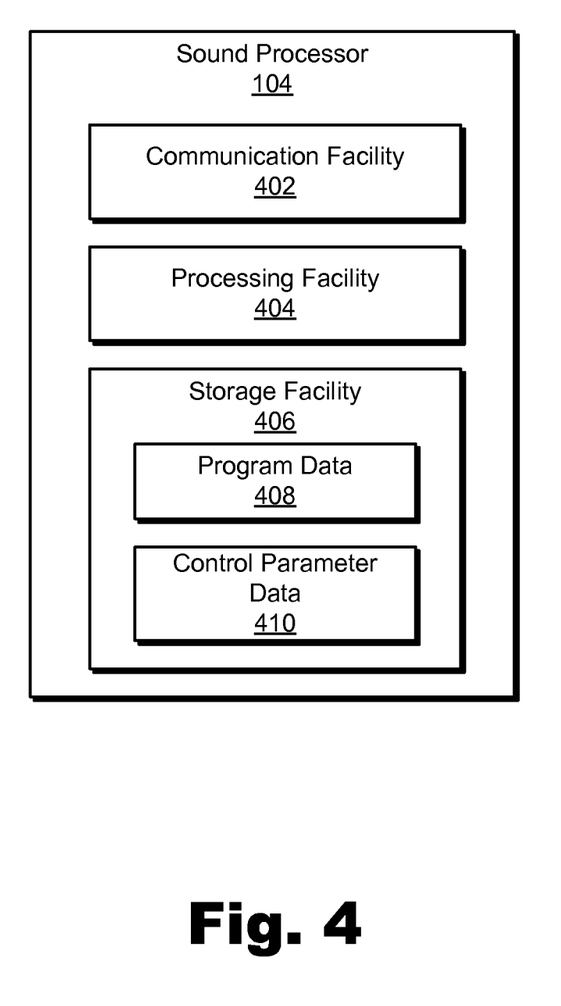
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and implantable cochlear stimulator 110. For example, communication facility 402 may include transceiver components configured to wirelessly transmit data (e.g., control parameters and/or power signals) to implantable cochlear stimulator 110 and/or wirelessly receive data from implantable cochlear stimulator 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of implantable cochlear stimulator 110 (e.g., one or more stimulation parameters defining the electrical stimulation to be generated and applied by implantable cochlear stimulator 110). In some examples, processing facility 404 may be configured to operate in accordance with one or more sound processing programs provided by fitting subsystem 202 and/or otherwise stored within storage facility 406.

Storage facility 406 may be configured to maintain program data 408 representative of one or more sound processing programs (which, in some examples, may be pre-loaded onto sound processor 104) and control parameter data 410 representative of one or more control parameters. Storage facility 406 may be configured to maintain additional or alternative data as may serve a particular implementation.

Figure 5:
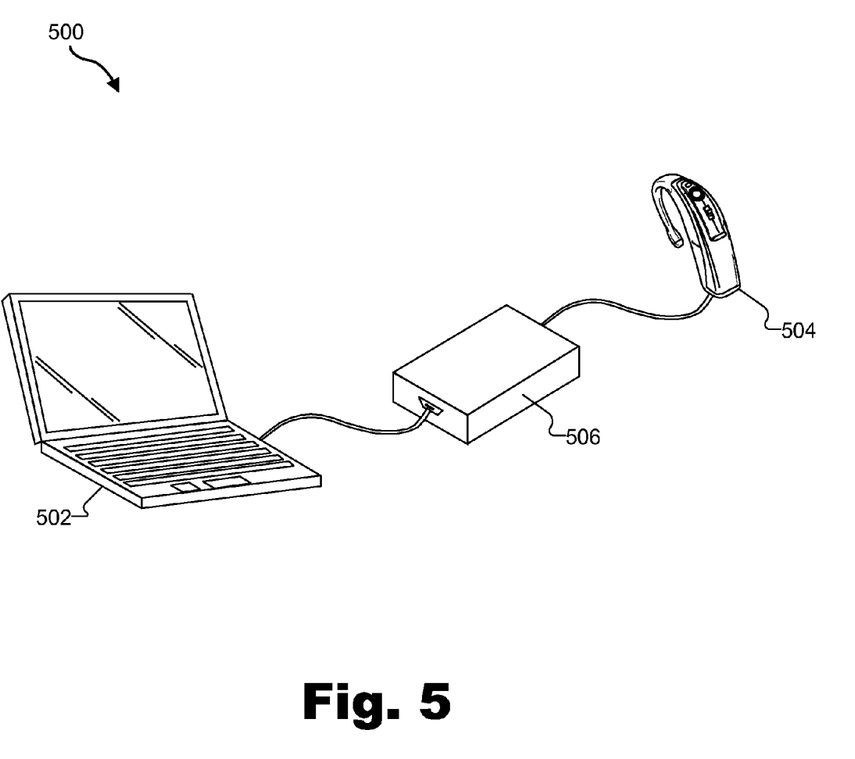
FIG. 5 illustrates an exemplary implementation of the cochlear implant fitting system of FIG. 2 according to principles described herein.

FIG. 5 illustrates an exemplary implementation 500 of fitting system 200. In implementation 500, a fitting station 502 may be selectively and communicatively coupled to a BTE unit 504 by way of a CPI device 506. BTE unit 504 is merely exemplary of the many different types of sound processors that may be used in accordance with the systems and methods described herein. Fitting station 502 may be selectively and communicatively coupled to any other type of sound processor as may serve a particular implementation.

Fitting station 502 may include any suitable computing device and/or combination of computing devices and be configured to perform one or more of the fitting operations described herein. For example, fitting station 502 may display one or graphical user interfaces configured to facilitate management of one or more patient data instances and/or archived patient data instances, selection of one or more sound processing programs by which BTE unit 504 operates, adjustment of one or more control parameters by which BTE unit 504 operates, and/or any other fitting operation as may serve a particular implementation. Fitting station 502 may be utilized by an audiologist, a clinician, and/or any other user to fit BTE unit 504 to a patient.

CPI device 506 may be configured to facilitate communication between fitting station 502 and BTE unit 504. In some examples, CPI device 506 may be selectively and communicatively coupled to fitting station 502 and/or BTE unit 504 by way of one or more ports included within fitting station 502 and BTE unit 504.

Figure 6:
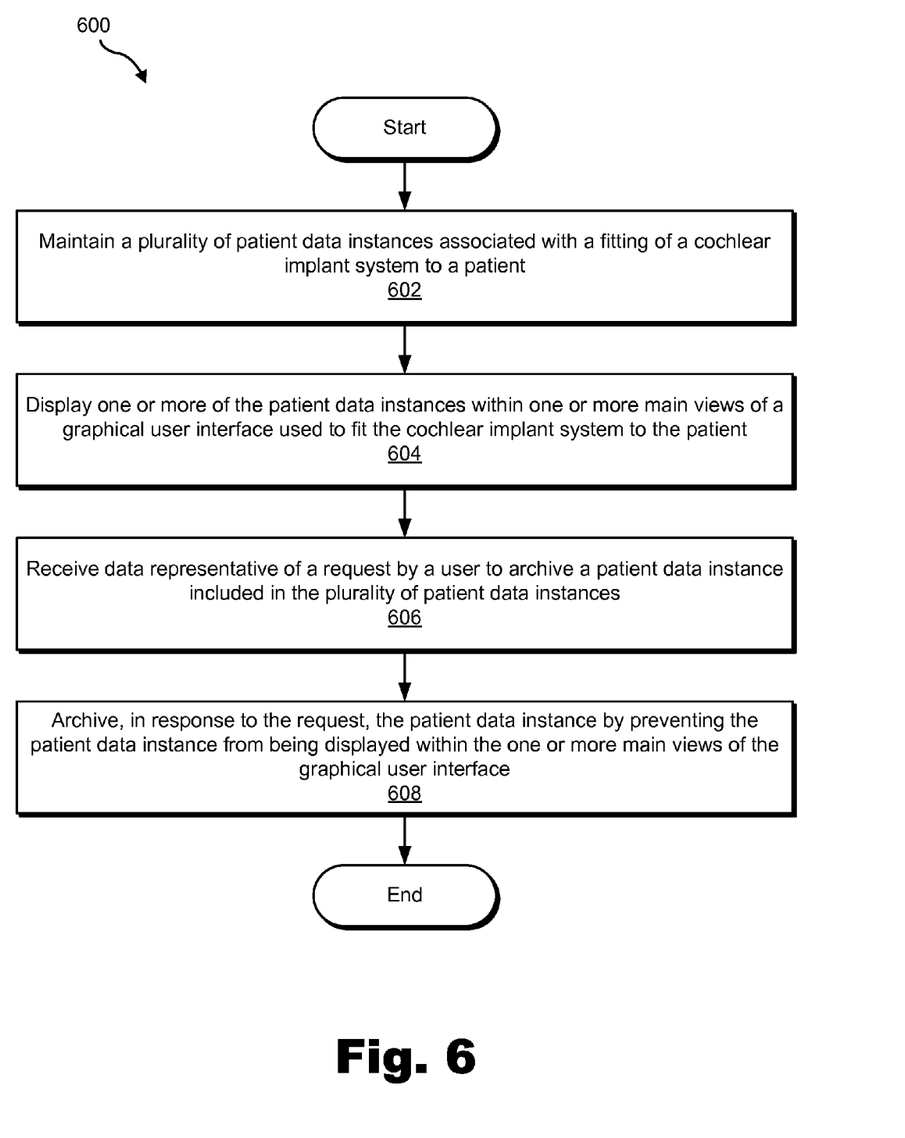
FIG. 6 illustrates an exemplary method of archiving patient data used to fit a cochlear implant system to a patient according to principles described herein.

FIG. 6 illustrates an exemplary method 600 of archiving patient data used to fit a cochlear implant system to a patient. While FIG. 6 illustrates exemplary steps according to one embodiment, other embodiments may omit, add to, reorder, and/or modify any of the steps shown in FIG. 6. One or more of the steps shown in FIG. 6 may be performed by any component or combination of components of fitting subsystem 202 and/or fitting station 502.

In step 602, a plurality of patient data instances associated with a fitting of a cochlear implant system to a patient are maintained. The plurality of patient data instances may be maintained in any of the ways described herein.

In step 604, one or more of the patient data instances are displayed within one or more main views of a graphical user interface used to fit the cochlear implant system to the patient. The one or more patient data instances may be displayed within one or more main views of a graphical user interface in any of the ways described herein.

Figure 7:
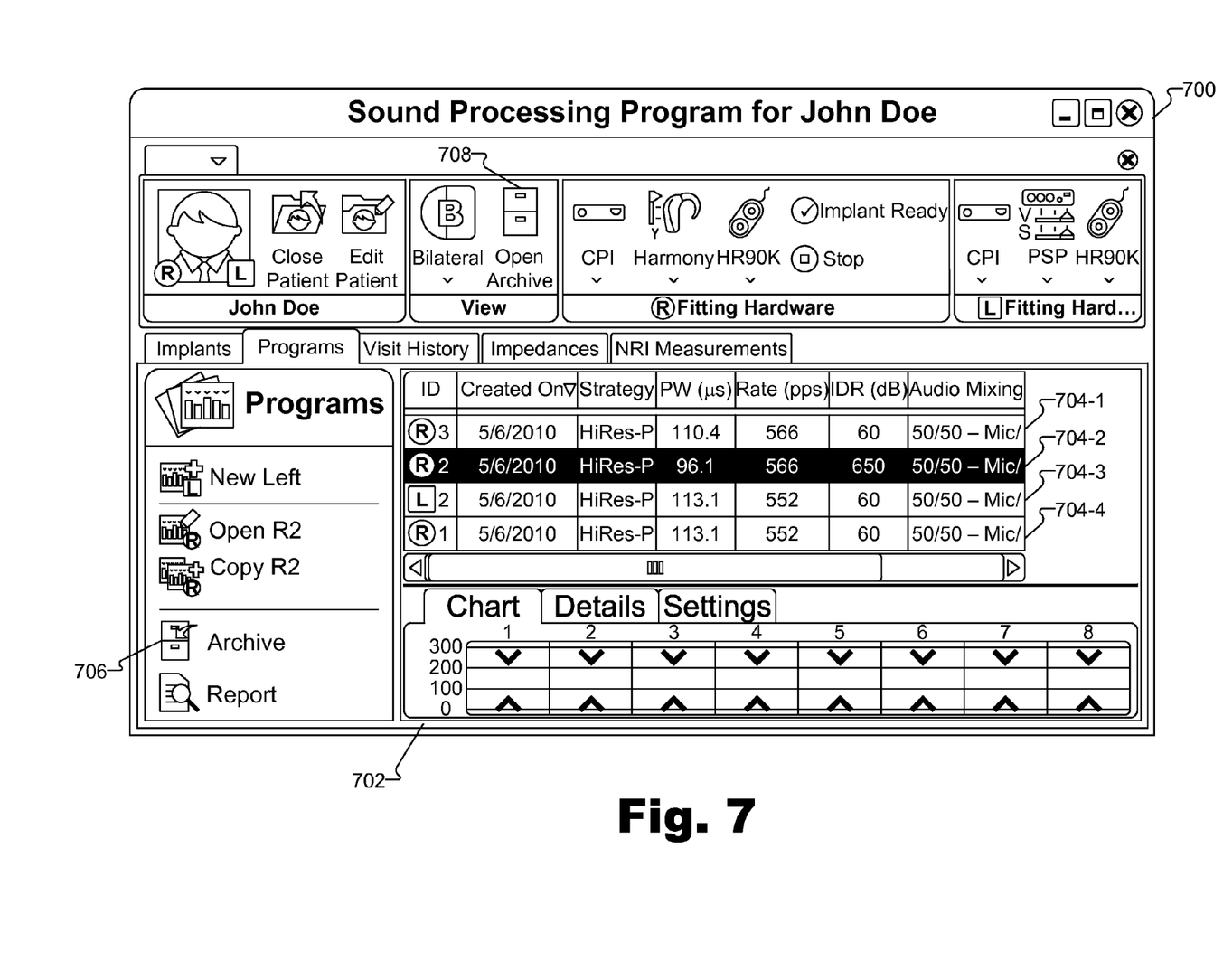
FIGS. 7-9 illustrate various views of an exemplary graphical user interface ("GUI") that may be displayed by a fitting subsystem according to principles described herein.

To illustrate, FIG. 7 shows an exemplary graphical user interface ("GUI") 700 that may be displayed by fitting subsystem 202. As shown in FIG. 7, a main view 702 may be displayed within GUI 700 that includes a plurality of patient data instances 704 (e.g., patient data instances 704-1 through 704-4). In the example of FIG. 7, each patient data instance 704 includes a row of program data associated with a distinct sound processing program used to fit a cochlear implant patient to a patient named "John Doe." In some examples, the values included in each patient data instance 704 may be edited by a user. It will be recognized that additional or alternative patient data instances may be displayed within main view 702 and/or within any other main view of GUI 700 as may serve a particular implementation.

Returning to FIG. 6, in step 606, data representative of a request by a user to archive a patient data instance included in the plurality of patient data instances is received by fitting subsystem 202. The request to archive a patient data instance may be received in any suitable manner as may serve a particular implementation.

To illustrate, in the example of FIG. 7, a user may select (e.g., highlight) a particular patient data instance 704 and then select an "archive" option 706 displayed within GUI 700 in order to request that the selected patient data instance be archived. For example, FIG. 7 shows that patient data instance 704-2 has been selected by a user. The user may then select "archive" option 706 to archive the selected patient data instance 704-2.

Returning to FIG. 6, in step 608, the patient data instance is archived in response to the request received in step 606 by preventing the patient data instance from being displayed within the one or more main views of the graphical user interface. The patient data instance may be prevented from being displayed within the one or more main views of the graphical user interface in any manner as may serve a particular implementation.

Figure 8:
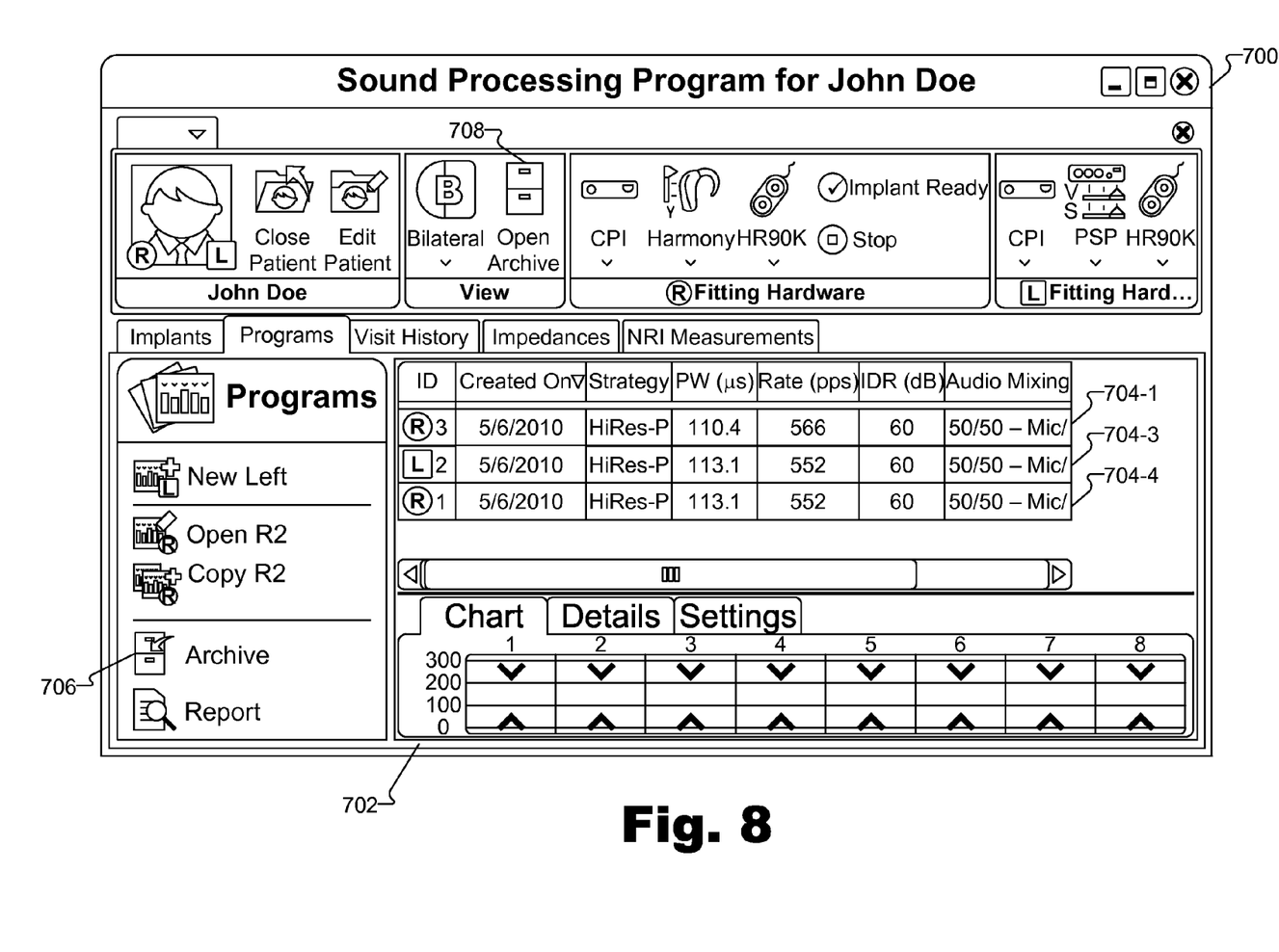

For example, patient data instance 704-2 shown in FIG. 7 may be removed from being displayed within main view 702 in response to a user selection of "archive" option 706. To illustrate, FIG. 8 shows GUI 700 after "archive" option 706 has been selected. As shown in FIG. 8, patient data instance 704-2 is no longer displayed within main view 702.

As mentioned, a patient data instance may be archived by preventing the patient data instance from being displayed in one or more main views of a graphical user interface. However, the patient data instance may still be maintained as patient data 312 by storage facility 310. In this manner, the patient data instance may be subsequently accessed by a user even though it is not displayed within the one or more main views of the graphical user interface.

In some examples, an archived patient data instance may be displayed in an archive view separate from the one or more main views of a graphical user interface. For example, an archive view including one or more archived patient data instances may be displayed within GUI 700 in response to user selection of an "open archive" option 708 included in GUI 700.

Figure 9:
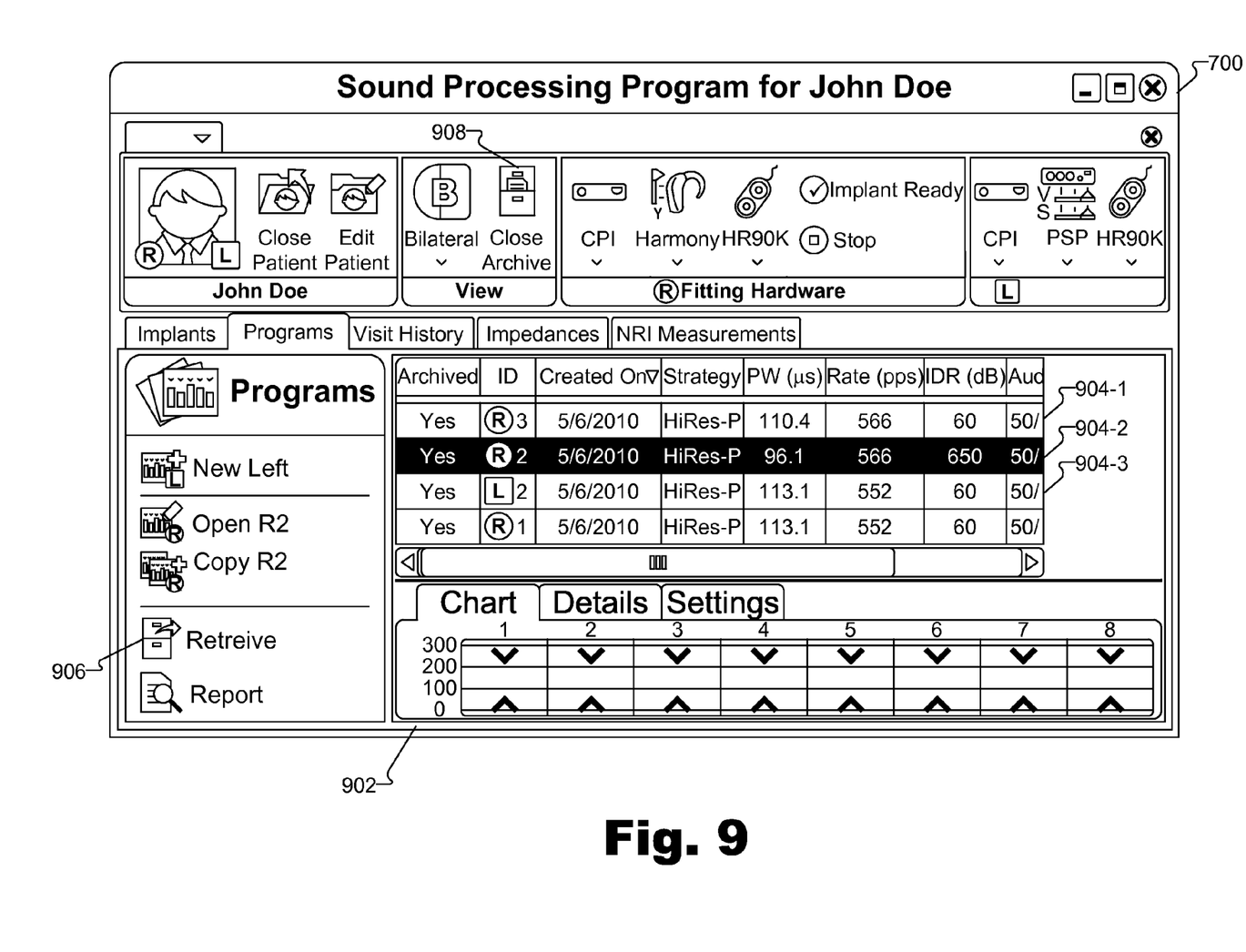

FIG. 9 shows an exemplary archive view 902 of GUI 700 that may be displayed in response to a user selection of "open archive" option 708. As shown in FIG. 9, a plurality of archived patient data instances 904 (e.g., patient data instances 904-1 through 904-4) may be displayed within archive view 902. In the example of FIG. 9, each archived patient data instance 904 includes a row of archived program data associated with a distinct sound processing program used to fit a cochlear implant patient to the patient named "John Doe." For example, archived patient data instance 904-2 is equivalent to the patient data instance 704-2 that was selected and archived in the example of FIG. 7.

The archived patient data instances displayed in archive view 902 may be used by fitting subsystem 202 to perform one or more fitting operations. For example, a user may select an archived patient data instance (e.g., archived patient data instance 904-2) and direct fitting subsystem 202 to perform a fitting operation in accordance with the selected archived patient data instance (e.g., direct sound processor 104 to operate in accordance with the sound processing program represented by the archived patient data instance.) Hence, one or more fitting operations may be initiated from either archive view 902 or main view 702.

In some examples, fitting subsystem 202 may allow a user to edit an archived patient data instance (e.g., archived patient data instance 904-2) while the archived patient data instance is displayed within archive view 902. For example, a user may edit one or more of the values included in archived patient data instance 904-2 while archived patient data instance 904-2 is displayed in archive view 902.

In some examples, a user may desire to unarchive an archived patient data instance. For example, a user may desire to unarchive archived patient data instance 904-2. To this end, the user may select (e.g., highlight) archived patient data instance 904-2, as shown in FIG. 9, and select a "retrieve" option 906 displayed in GUI 900. In response to the selection of the "retrieve" option 906, fitting subsystem 202 may unarchive archived patient data instance 904-2 by allowing the archived patient data instance 904-2 to again be displayed within main view 702 of GUI 700. For example, the archived patient data instance 904-2 may be displayed within main view 702 as patient data instance 704-2, as illustrated in FIG. 7. To access main view 702 of GUI 700 from the archive view 902 of FIG. 9, a "close archive" option 908 may be selected by the user.

Figure 10:
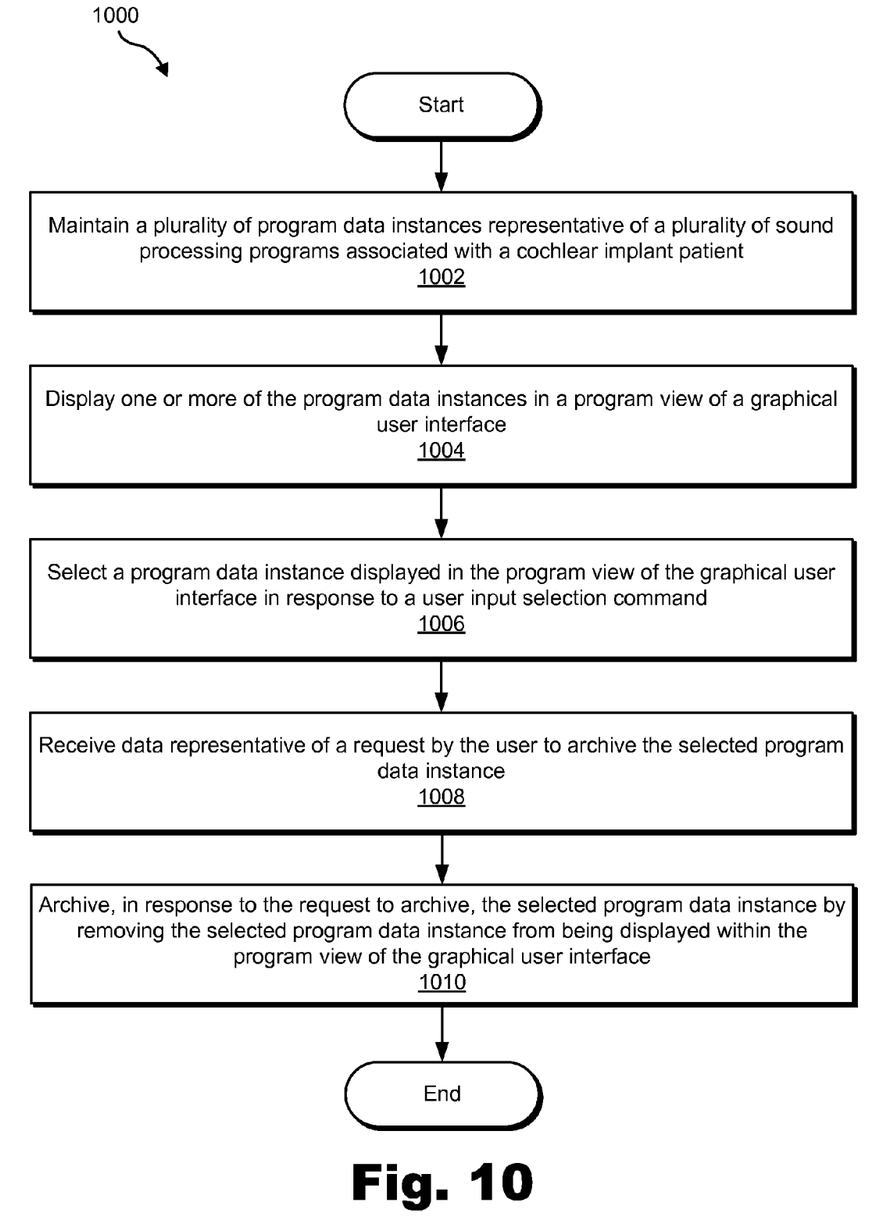
FIG. 10 illustrates another exemplary method of archiving patient data used to fit a cochlear implant system to a patient according to principles described herein.

FIG. 10 illustrates another exemplary method 1000 of archiving patient data used to fit a cochlear implant system to a patient. While FIG. 10 illustrates exemplary steps according to one embodiment, other embodiments may omit, add to, reorder, and/or modify any of the steps shown in FIG. 10. One or more of the steps shown in FIG. 10 may be performed by any component or combination of components of fitting subsystem 202 and/or fitting station 502.

In step 1002, a plurality of program data instances representative of a plurality of sound processing programs associated with a cochlear implant patient are maintained. The program data instances may be included in patient data 312 maintained by storage facility 310, for example.

In step 1004, one or more of the program data instances are displayed in a program view of a graphical user interface. The program view may include or be similar to main view 702 shown in FIGS. 7 and 8, for example. The program view may alternatively include any other view of a graphical user interface used to fit a cochlear implant system to a patient other than an archive view as may serve a particular implementation.

In step 1006, a program data instance displayed in the program view of the graphical user interface is selected in response to a user input selection command. The program data instance may be selected in any suitable manner as may serve a particular implementation.

In step 1008, data representative of a request by the user to archive the selected program data instance is received. The data may be received in any suitable manner as may serve a particular implementation.

In step 1010, the selected program data instance is archived, in response to the request to archive, by removing the selected program data instance from being displayed within the program view of the graphical user interface. The selected program data instance may be removed from being displayed within the program view in any suitable manner as may serve a particular implementation.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 11:
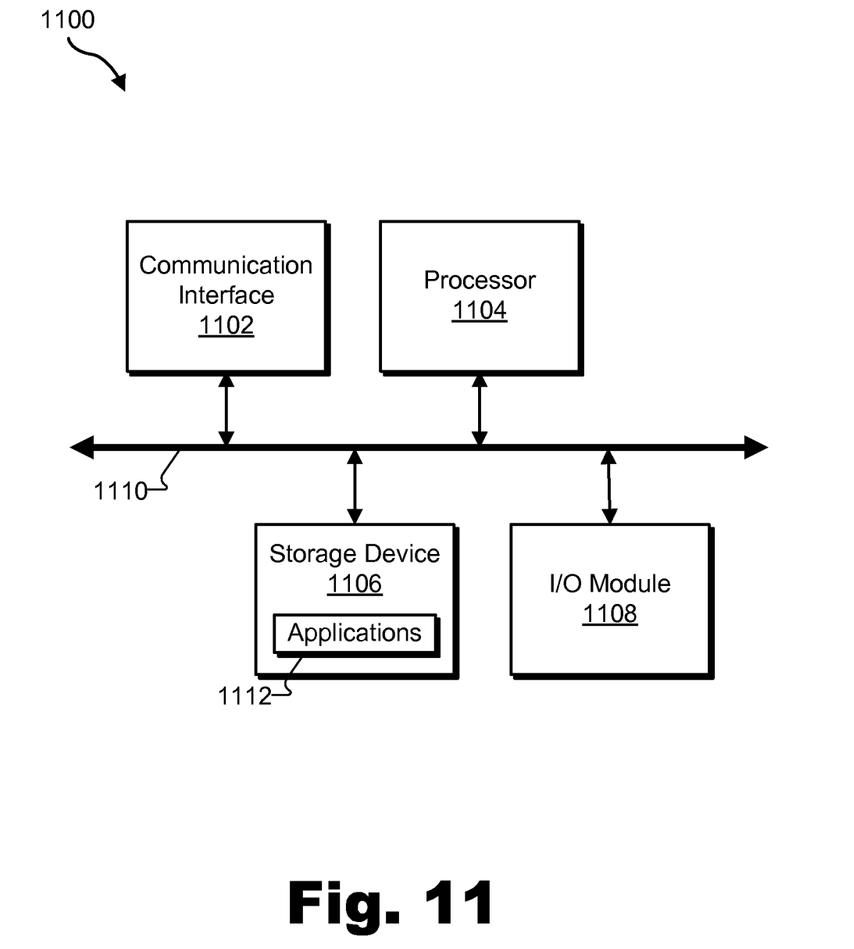
FIG. 11 illustrates an exemplary computing device according to principles described herein.

FIG. 11 illustrates an exemplary computing device 1100 that may be configured to perform one or more of the processes described herein. As shown in FIG. 11, computing device 1100 may include a communication interface 1102, a processor 1104, a storage device 1106, and an input/output ("I/O") module 1108 communicatively connected via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, and any other suitable interface. Communication interface 1102 may additionally or alternatively provide such a connection through, for example, a local area network (such as an Ethernet network), a personal area network, a telephone or cable network, a satellite data connection, a dedicated URL, or any other suitable connection. Communication interface 1102 may be configured to interface with any suitable communication media, protocols, and formats, including any of those mentioned above.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another non-transitory computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1106. For example, data representative of one or more executable applications 1112 (which may include, but are not limited to, one or more of the software applications described herein) configured to direct processor 1104 to perform any of the operations described herein may be stored within storage device 1106. In some examples, data may be arranged in one or more databases residing within storage device 1106.

I/O module 1108 may be configured to receive user input and provide user output and may include any hardware, firmware, software, or combination thereof supportive of input and output capabilities. For example, I/O module 1108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1108 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1100. For example, one or more applications 1112 residing within storage device 1106 may be configured to direct processor 1104 to perform one or more processes or functions associated with communication facility 302, user interface facility 304, fitting facility 306, archive facility 308, communication facility 402, and/or processing facility 404. Likewise, storage facility 310 and/or storage facility 406 may be implemented by or within storage device 1106.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. A method comprising:
   maintaining, by a fitting subsystem, a plurality of patient data instances associated with a fitting of a cochlear implant system to a patient;

displaying, by the fitting subsystem, one or more of the patient data instances within one or more main views of a graphical user interface used to fit the cochlear implant system to the patient;

receiving, by the fitting subsystem, data representative of a request by a user to archive a patient data instance included in the plurality of patient data instances;

archiving, by the fitting subsystem in response to the request, the patient data instance by preventing the patient data instance from being displayed within the one or more main views of the graphical user interface;

receiving, by the fitting system, data representative of a request by the user to view the archived patient data instance; and displaying, by the fitting subsystem in response to the request to view the archived patient data instance, the archived patient data instance within an archive view of the graphical user interface, the archive view being separate from the one or more main views of the graphical user interface.

2. The method of claim 1, further comprising allowing, by the fitting subsystem, the user to edit the archived patient data instance while the archived patient data instance is displayed within the archive view.

3. The method of claim 1, further comprising:
receiving, by the fitting system, data representative of a request by a user to perform a fitting operation using the archived patient data instance; and
utilizing, by the fitting subsystem, the archived patient data instance to perform the requested fitting operation.

4. The method of claim 1, further comprising:
receiving, by the fitting system, data representative of a request by a user to unarchive the archived patient data instance; and
unarchiving, by the fitting subsystem in response to the request to unarchive the archived patient data instance, the archived patient data instance by allowing the archived patient data instance to be displayed within the one or more main views of the graphical user interface.

5. The method of claim 1, wherein the plurality of patient data instances comprises one or more program data instances representative of one or more sound processing programs associated with the patient.

6. The method of claim 1, wherein the plurality of patient data instances comprises data representative of cochlear implant records associated with the patient.

7. The method of claim 1, wherein the plurality of patient data instances comprises measurement data representative of one or more measurements performed by the cochlear implant system.

8. The method of claim 1, further comprising:
displaying, by the fitting subsystem, an archive option within the graphical user interface;
wherein the receiving of the data representative of the request by the user to archive the patient data instance comprises detecting a selection by the user of the archive option.

9. The method of claim 1, embodied as computer-executable instructions on at least one non-transitory computer-readable medium.

10. A method comprising:
maintaining, by a fitting subsystem, a plurality of program data instances representative of a plurality of sound processing programs associated with a cochlear implant patient;

displaying, by the fitting subsystem, one or more of the program data instances in a program view of a graphical user interface;

selecting, by the fitting subsystem, a program data instance displayed in the program view of the graphical user interface in response to a user input selection command;

receiving, by the fitting subsystem, data representative of a request by a user to archive the selected program data instance;

archiving, by the fitting subsystem in response to the request to archive, the selected program data instance by removing the selected program data instance from being displayed within the program view of the graphical user interface;

receiving, by the fitting subsystem, data representative of a request by the user to view the archived program data instance; and displaying, by the fitting subsystem in response to the request to view the archived program data instance, the archived program data instance within an archive view of the graphical user interface, the archive view being separate from one or more main views of the graphical user interface.

11. The method of claim 10, further comprising:
receiving, by the fitting system, data representative of a request by a user to perform a fitting operation using the archived program data instance; and
utilizing, by the fitting subsystem, the archived program data instance to perform the requested fitting operation.

12. The method of claim 10, further comprising:
receiving, by the fitting system, data representative of a request by a user to unarchive the archived program data instance; and
unarchiving, by the fitting subsystem in response to the request to unarchive the archived program data instance, the archived program data instance by allowing the archived program data instance to be displayed within the one or more main views of the graphical user interface.

13. The method of claim 10, further comprising:
displaying, by the fitting subsystem, an archive option within the graphical user interface;
wherein the receiving of the data representative of the request by the user to archive the program data instance comprises detecting a selection by the user of the archive option.

14. The method of claim 10, embodied as computer-executable instructions on at least one non-transitory computer-readable medium.

15. A system comprising:
a storage facility configured to maintain a plurality of patient data instances associated with a fitting of a cochlear implant system to a patient;
a user interface facility communicatively coupled to the storage facility and configured to display one or more of the patient data instances within one or more main views of a graphical user interface used to fit the cochlear implant system to the patient; and
an archive facility communicatively coupled to the storage facility and to the user interface facility and configured to
receive data representative of a request by a user to archive a patient data instance included in the plurality of patient data instances,
archive, in response to the request, the patient data instance by preventing the patient data instance from being displayed within the one or more main views of the graphical user interface, and receive data representative of a request by the user to view the archived patient data instance, wherein the user interface facility is further configured to display, in response to the request to view the archived patient data instance, the archived patient data instance within an archive view of the graphical user interface, the archive view being separate from the one or more main views of the graphical user interface.

16. The system of claim 15, wherein the archive facility is further configured to:

receive data representative of a request by a user to perform a fitting operation using the archived patient data instance; and utilize the archived patient data instance to perform the requested fitting operation.

17. The system of claim 15, wherein the archive facility is further configured to:

receive data representative of a request by a user to unarchive the archived patient data instance; and unarchive, in response to the request to unarchive the archived patient data instance, the archived patient data instance by allowing the archived patient data instance to be displayed within the one or more main views of the graphical user interface.

* * * * *